United States Patent [19]

Je

[11] Patent Number: 5,459,445
[45] Date of Patent: Oct. 17, 1995

[54] ELECTROMAGNETIC WAVE REDUCTION DEVICE

[76] Inventor: Jung H. Je, No. 303 San-ho Apartment, Suan-dong Dong-rae Gu, Pusan, Rep. of Korea

[21] Appl. No.: 259,075

[22] Filed: Jun. 13, 1994

[51] Int. Cl.⁶ ..................................................... H01J 1/52
[52] U.S. Cl. .......................... 335/214; 335/212; 335/301; 335/210; 315/85
[58] Field of Search ...................................... 335/210–214, 335/302–306; 313/440; 315/8, 85; 600/9, 15; 123/538; 210/222

[56] References Cited

U.S. PATENT DOCUMENTS

| | | | |
|---|---|---|---|
| 4,549,532 | 10/1985 | Baermann | 128/1.3 |
| 4,713,589 | 12/1987 | Kashiwagi | 315/400 |
| 5,063,368 | 11/1991 | Ettehadieh | 335/301 |

*Primary Examiner*—Leo P. Picard
*Assistant Examiner*—Ramon M. Barrera

[57] ABSTRACT

The present invention is a device to reduce the electromagnetic waves generated by electric appliances with surface displays including but not limited to computer monitors and televisions. Further, the electromagnetic waves can be reduced in electronic products generating high heat including, but not limited to, microwave ovens if the device is installed where the heat does not affect the strength of the magnet. The device, made up of several magnet joined together by joining opposite poles, reduces electromagnetic wave emission, and further, its strength affects the blood stream of the human being in vicinity of the device increasing the ions in the body and helps disposing of the food waste in the human body to enhance the metabolism.

4 Claims, 8 Drawing Sheets

ELECTROMAGNETIC WAVE REDUCTION DEVICE

FIELD OF THE INVENTION

The present invention generally relates to a magnetic device, particularly to a magnetic device which reduces the electromagnetic wave emission of electric appliances including but not limited to computer monitors and televisions.

BACKGROUND OF THE INVENTION

It is a commonly known fact that computer monitors and televisions emit electromagnetic waves. These electromagnetic waves have been determined and proven to be hazardous to human health. Cataracts, insomnia, headaches, and tiredness are some of the symptoms and side effects which have been attributed to exposure to the electromagnetic waves emitted from televisions with screens of twenty-five (25) inches or larger.

The electromagnetic waves produced by cathode ray tubes (CRTs) housed within computer monitors and televisions are emitted through the viewing screen, top portion, sides, and rear portion of the monitor or television. In order to reduce the emission of harmful electromagnetic waves, methods have been devised and utilized such as coating the circumference of electronic guns housed within said devices with high frequency-resistant metals, as well as coating the viewing screen to absorb the electromagnetic waves. Both preventing and absorbing the emission of electromagnetic waves, however, are extremely difficult, and the effectiveness of the above mentioned methods decrease as the amount of wave emission increases.

Furthermore, there are limitations to how much wave emission can be absorbed and reduced, and the cost to install such preventive devices is so high that it has become sensible to install the devices only on computer monitors that are required by law to have such wave reducing protective coatings.

SUMMARY OF THE INVENTION

The present invention solves the problems discussed above by absorbing electromagnetic waves near the source of their production. Furthermore, the present invention is relatively inexpensive to manufacture and easy to install.

The presently invented device is comprised of at least four magnets joined in a certain configuration. It is designed to be installed next to the source of electromagnetic wave production in electric appliances including but not limited to televisions and computer monitors.

Furthermore, the magnetic strength of the presently invented device positively affects the blood stream of human beings in the vicinity, increasing ions and enhancing metabolism by helping to dispose of food wastes.

Thus, it is a primary object of the present invention to reduce the amount of electromagnetic waves emitted from electric appliances with surface displays including but not limited to computer monitors and televisions;

it is a further object of the present invention to be installed to the source of wave emission rather than attempting to absorb the waves from the outer surface of said electric appliances;

it is still a further object of the present invention to provide at least four magnets joined in a specific configuration which comprise the present invention.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 6 is a view of the present invention attached to the front of the display screen shown in FIG. 5; and FIG. 7 is a view of the present invention attached to the back of the display screen shown in FIG. 5.

DETAILED DESCRIPTION OF THE PREFERRED EMBODIMENT

Figure 8:
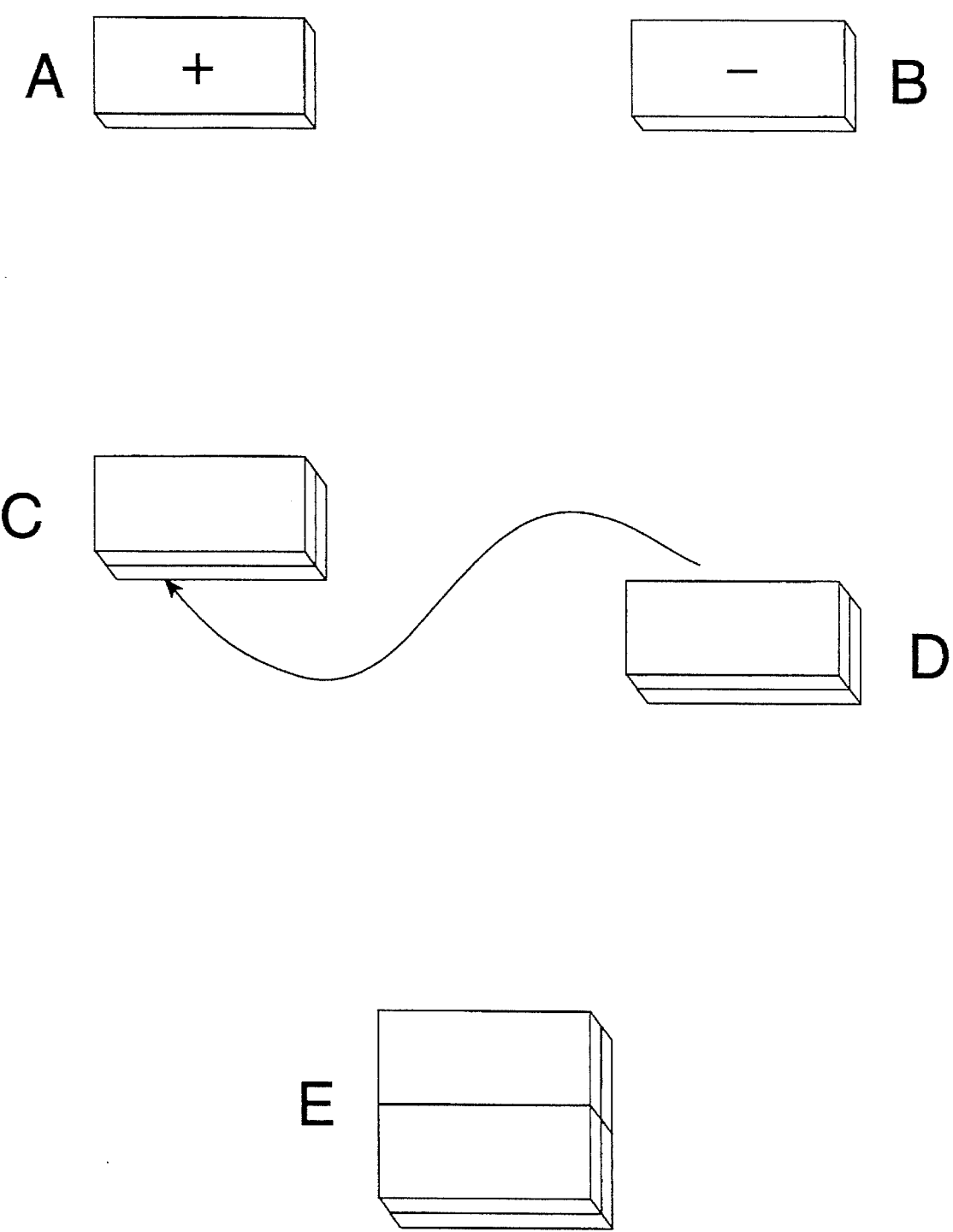
FIG. 8 is a top view of the present invention, demonstrating how it is formed from at least four permanent magnets.

Referring now to FIG. 8, two magnets A and B are shown. These magnets are permanent magnets, each having a length of two (2) centimeters, width of one and one-tenth (1.1) centimeters, and height of five-tenths (0.5) of a centimeter. These measurements, of course, may be modified as the need arises. The sides of these permanent magnets will hereinafter be referred to as the flat side (length×width), the long height side (height×length), and the short height side (height×width).

The positively charged flat side of permanent magnet A is naturally attracted to the negatively charged flat side of permanent magnet B, thereby forming permanent magnet C. Permanent magnet C is then joined by its long height side to the long height side of a similarly formed permanent magnet D.

The magnet thereby formed E is the building block of the present invention: one permanent magnet formed by joining four separate permanent magnets in the above-described manner. This magnet formed by joining four separate magnets will hereinafter be referred to as "building block". Many of these building blocks can be further joined together by both their long height sides and short height sides. The strength and effectiveness of the magnet increase as more building blocks are added. This expandable magnet, comprised of at least one building block, will hereinafter be referred to as "joined permanent magnet".

When magnets of different formation than the present invention are moved close to the electronic guns of computers and televisions, the screens of said appliances often become disordered. Tests have proven that the presently invented joined permanent magnet restores order to screens which have been disordered in such a way. Disordered screens can also be set straight when two magnets of weaker strength are joined and brought near to said electronic guns, but the effect of the electromagnetic field generated by such a magnet is limited, and the heat generated by the electronic gun decreases the intensity of its magnetic strength.

Figure 1:
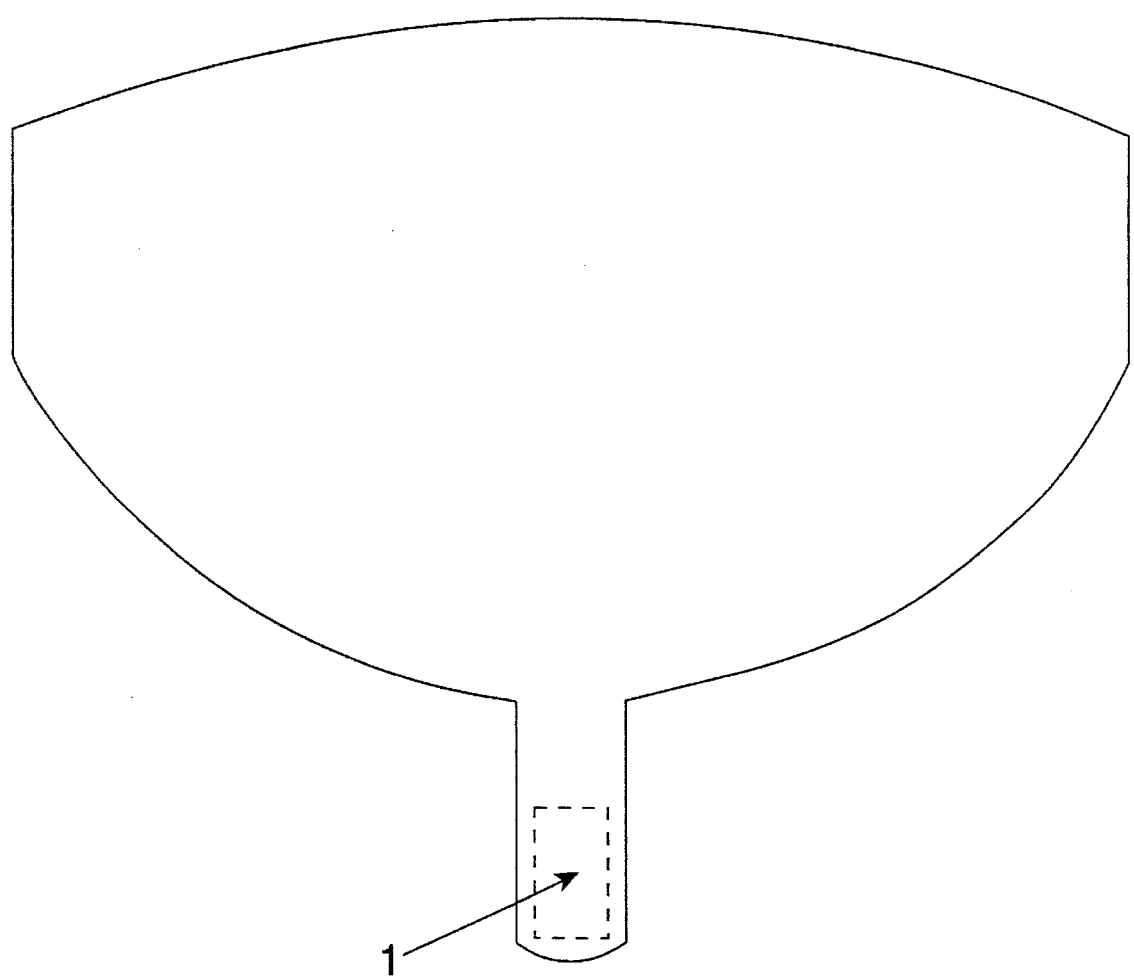
FIG. 1 is a top view of a cathode ray tube (CRT)
Figure 2:
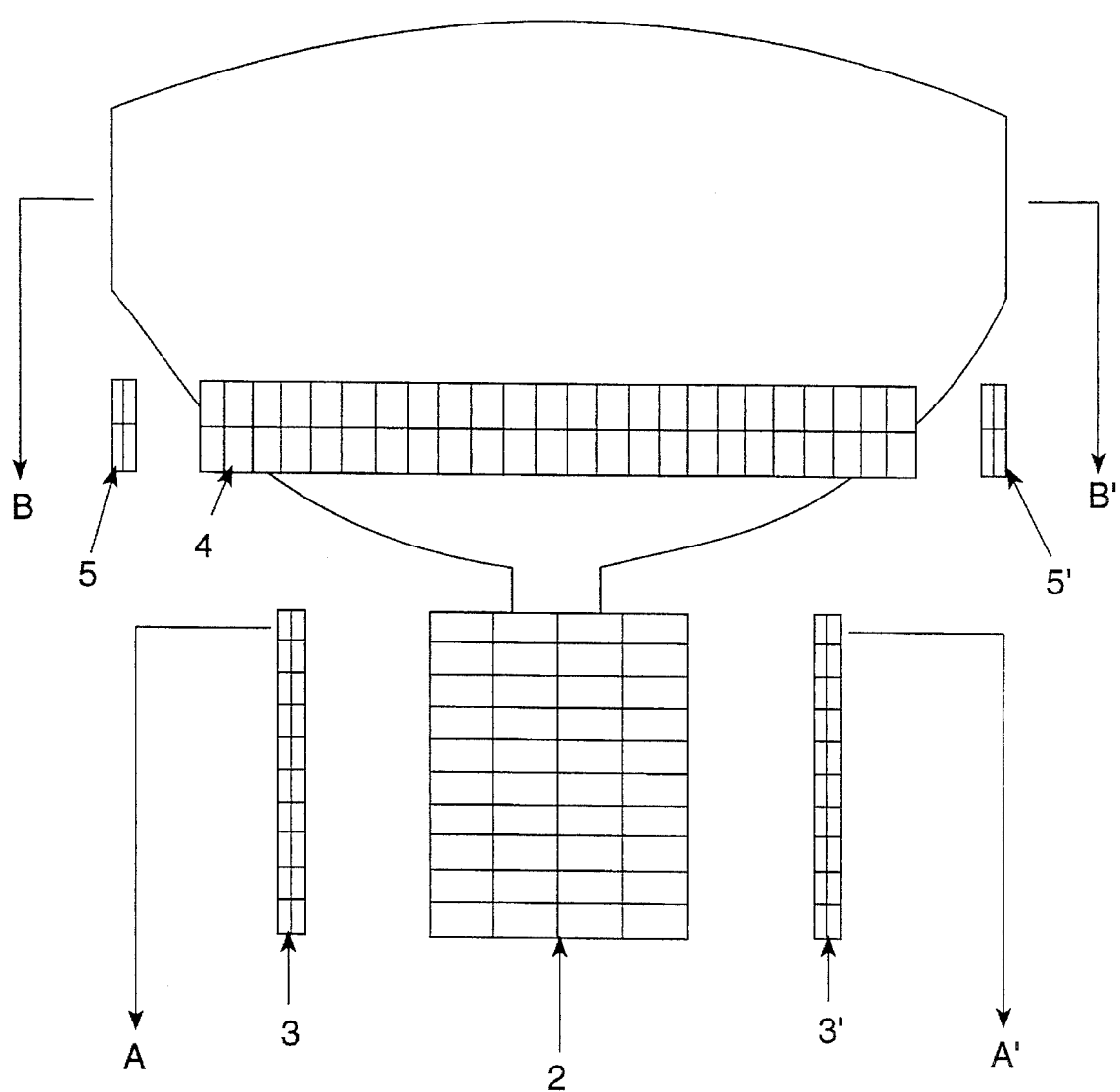
FIG. 2 is a view of the presently invented device installed around the cathode ray tube shown in FIG. 1.

Referring to FIG. 1, a top view of a cathode ray tube is shown with an electronic gun 1 installed in the rear portion. FIG. 2 shows the cathode ray tube shown in FIG. 1 surrounded by joined permanent magnets 2, 3, 3', 4, 5, and 5'.

Figure 3:
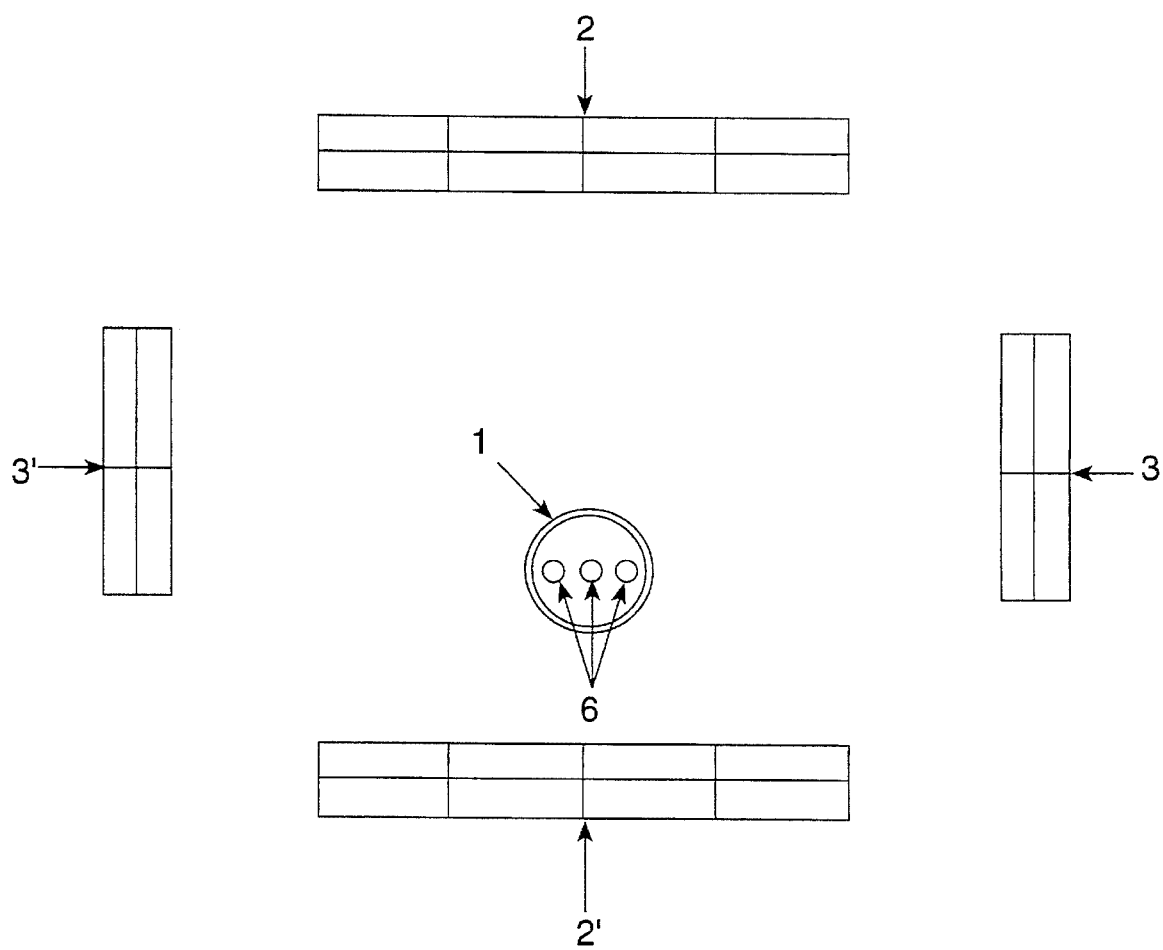
FIG. 3 is an exploded frontal view of A—A' of FIG. 2.
Figure 4:
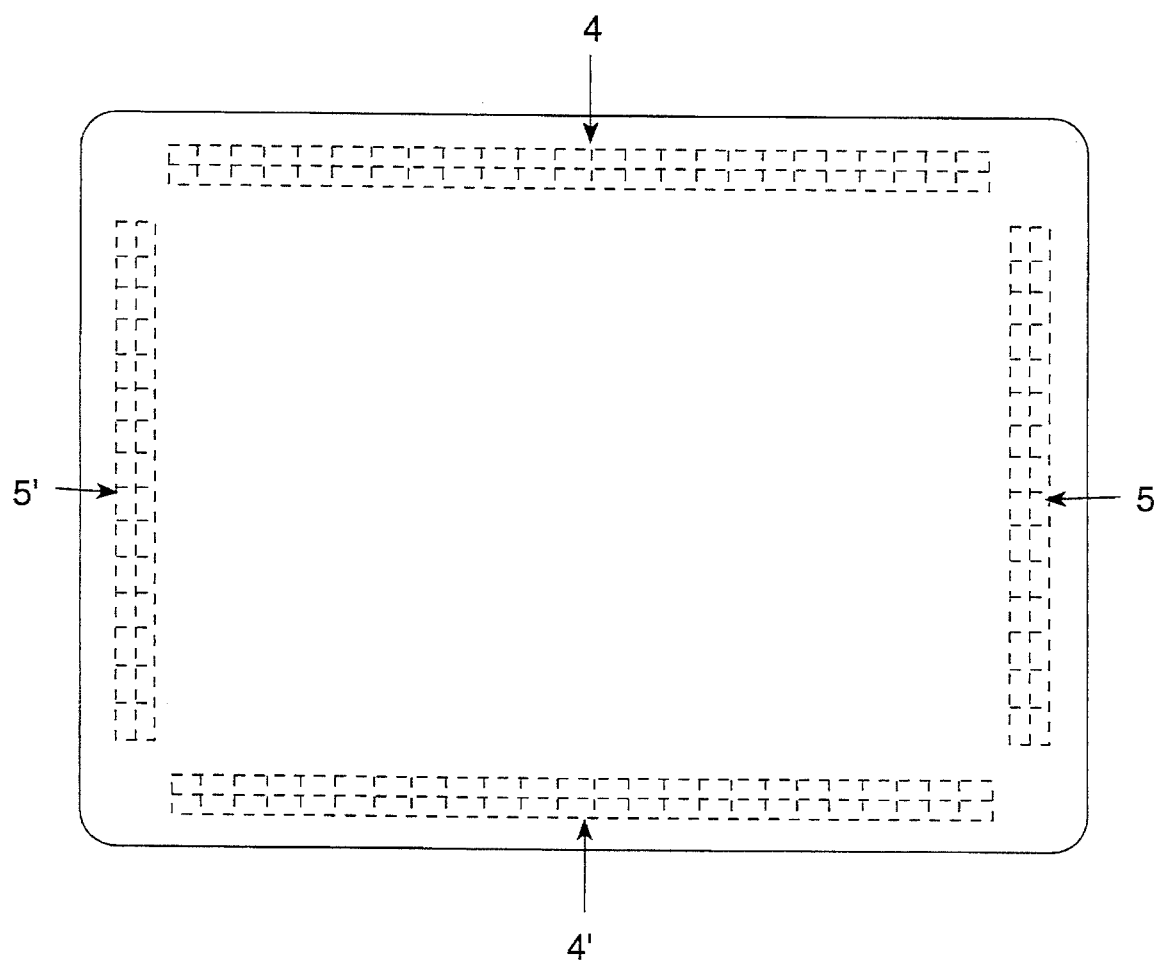
FIG. 4 is an exploded frontal view of B—B' of FIG. 2.

Joined permanent magnets 2, 3, 3', and 2', shown in FIG. 3, are installed around the electronic gun 1. The number of building blocks used to form the joined permanent magnets may be increased or decreased according to the size of the electronic gun. Joined permanent magnets 4, 5, and 5', and 4', shown in FIG. 4, are installed around the deflection coil. The installation methods resulting in the most effectiveness are shown in FIG. 2.

Moving one single permanent magnet near to the deflection coil causes both a lopsided picture and green and red colored dots to appear on the corners of the screen. The screen returns to normal, however, when the single permanent magnet is affixed to three other single permanent magnets, forming the present invention, and brought close to the deflection coil. This action also changes the green and red colors on the screen back to their normal settings.

When positive and negative charges of electricity are supplied to the electronic gun 1 of the cathode ray tube shown in FIG. 3, electronic beams 6 are shot toward the viewing screen, creating both an electric and magnetic field. Displays including but not limited to Liquid Crystal Displays, Luminescent Electronic Diodes, Plasma Displays, Video Frequency Displays, and Electro Luminescent Displays similarly use positive and negative charges of electricity.

Figure 5:
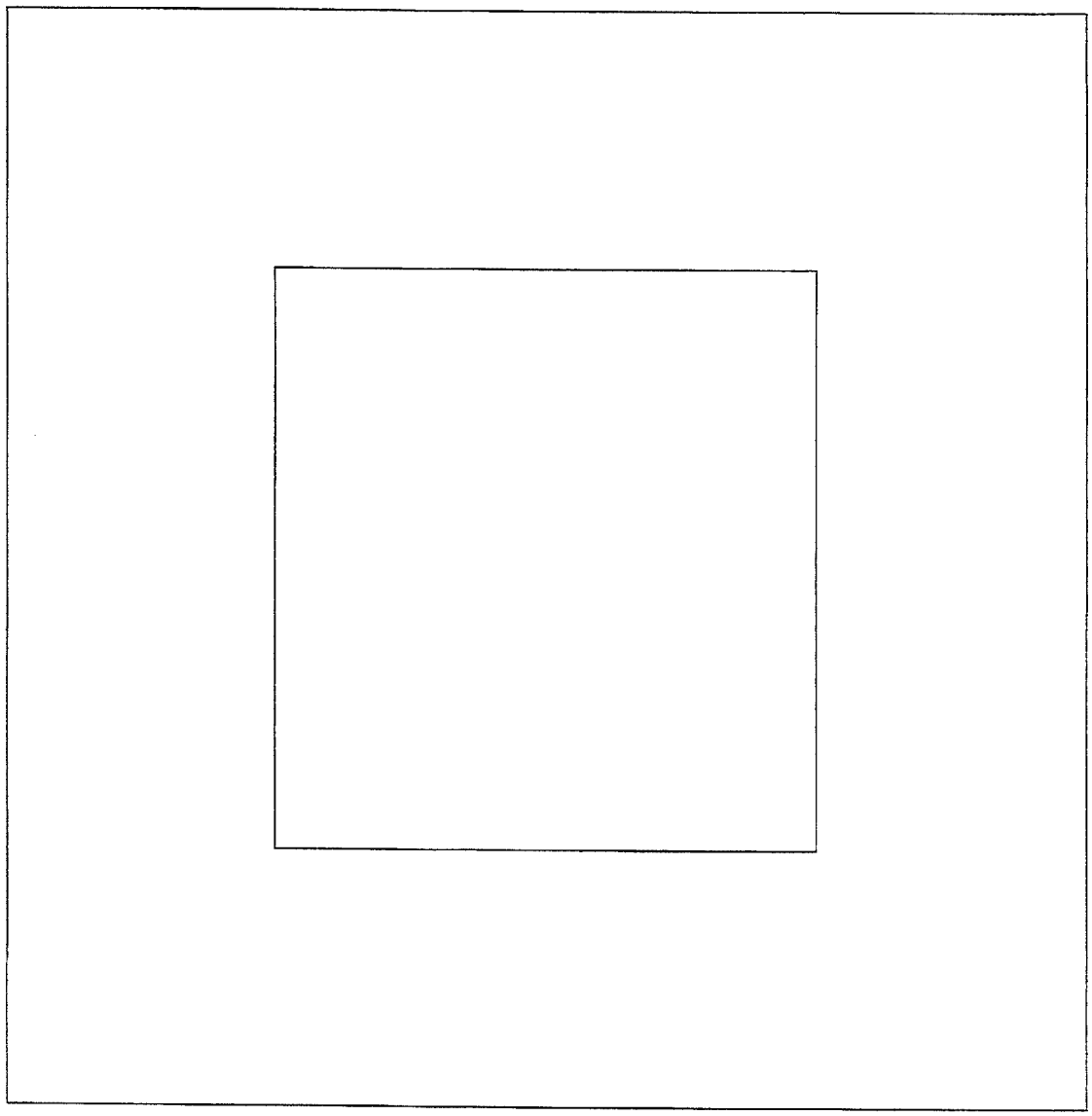
FIG. 5 is a frontal view of a display screen.

As these positive and negative charges of electricity are projected to the display screen, shown in FIG. 5, an electric field, magnetic field, electric magnetic field, and electromagnetic waves are generated. The electric field and magnetic field interact to become an electromagnetic field, and within the electromagnetic field a cycle of changes occurs causing systematic waves of both the electric field and the magnetic field to spread out. These waves are referred to as electromagnetic waves.

Figure 6:
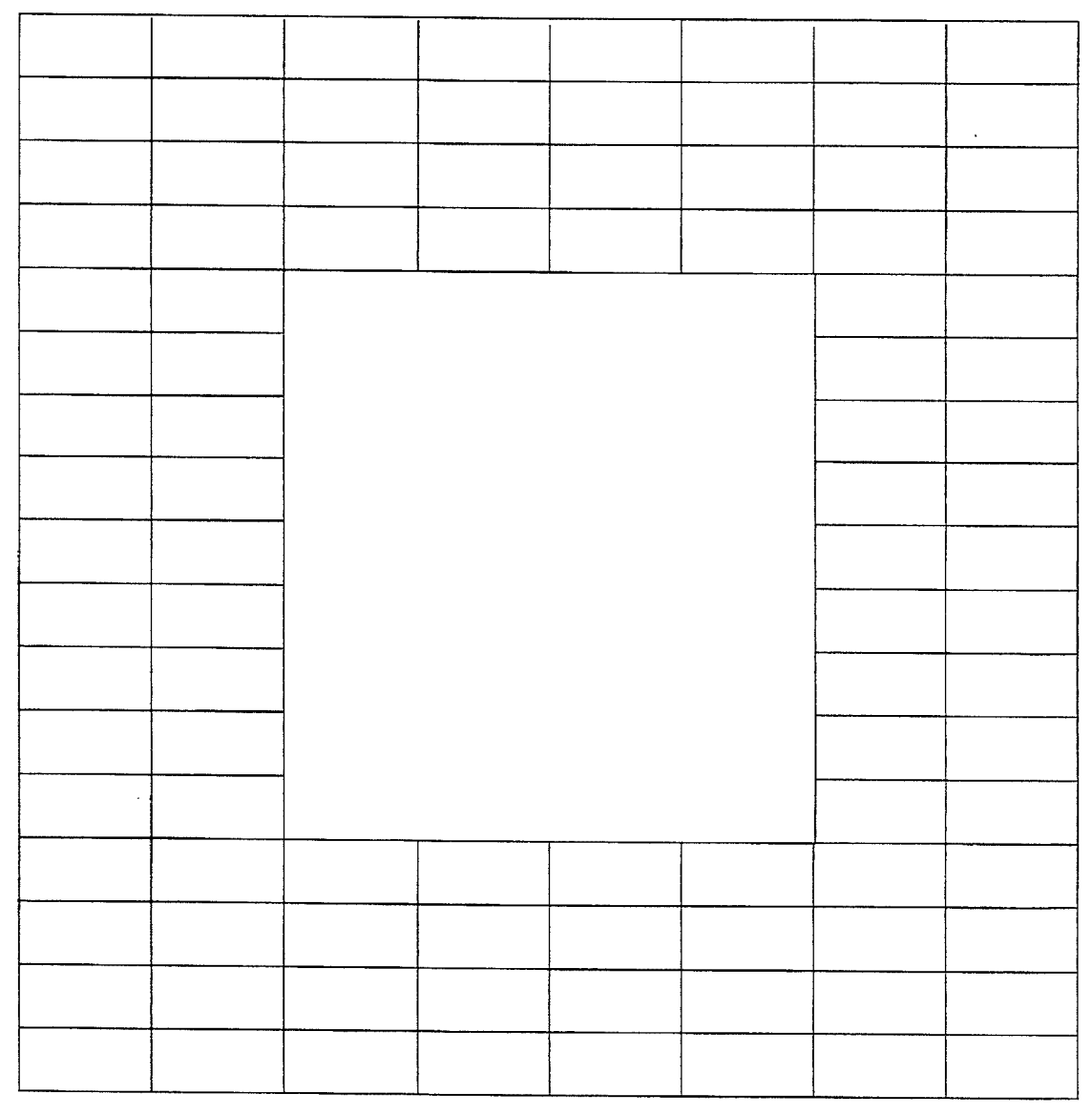
Figure 7:
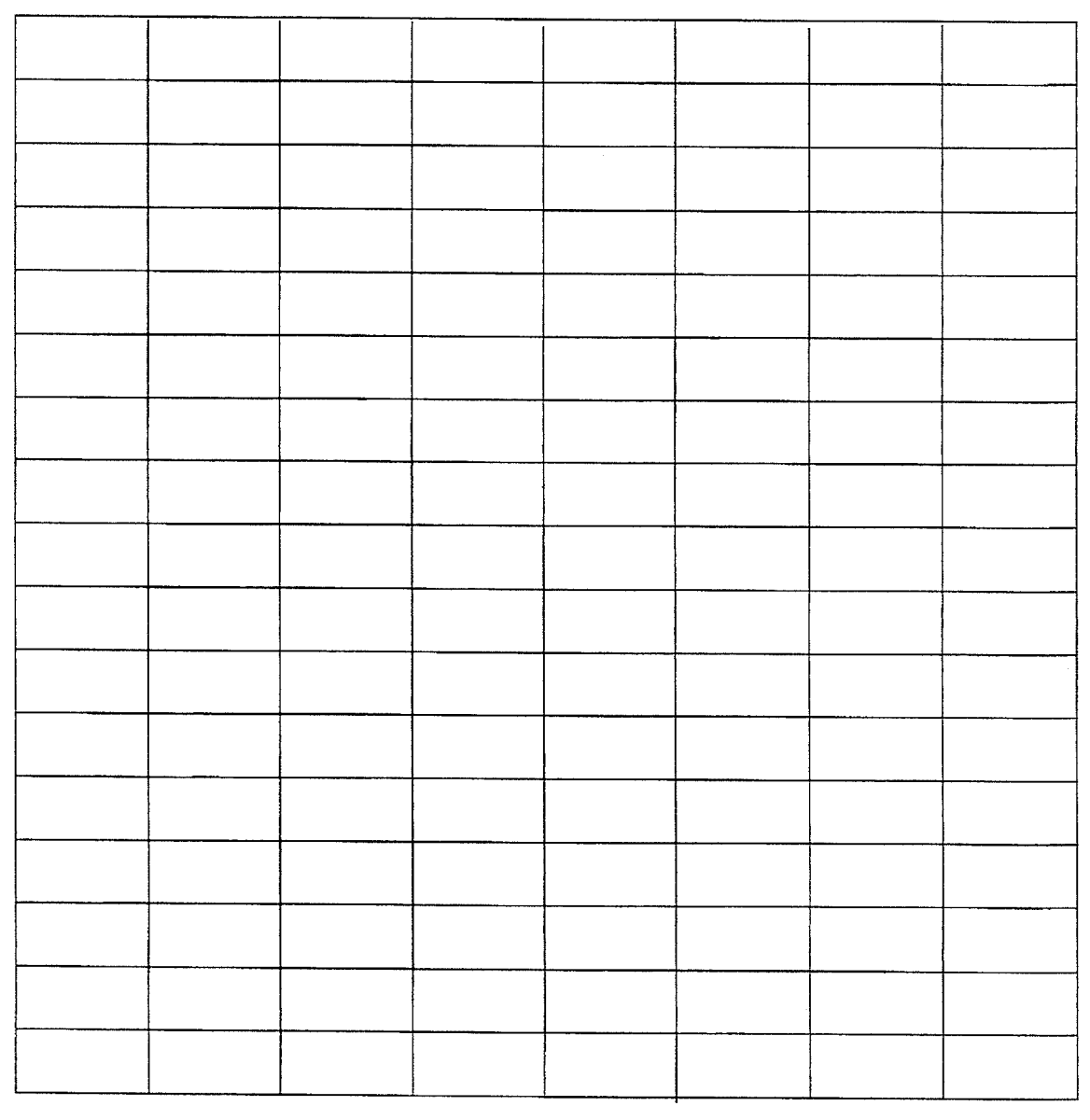

The presently invented joined permanent magnets are further installed around the front of the display screen, as shown in FIG. 6, as well as covering the entire back side, as shown in FIG. 7. These magnets further reduce electromagnetic waves which are generated at the screen.

Thus, the present invention not only reduces the electromagnetic waves emitted from the electronic gun and the deflection coil of a computer monitor or television, but it reduces electromagnetic wave emission from the screen of said devices as well.

Furthermore, the presently invented magnet can be inserted into a plastic case with self-adhesive means attached to the outer surface. This self-adhesive means allows attachment of the plastic case to the outer surface of a computer monitor or television, which greatly reduces the cost of installation. This method of installation also allows convenient attachment of the present invention to pre-assembled computer monitors and television sets which would otherwise be very difficult to disassemble for installation.

As to the manner of usage and operation of the present invention, the same should be apparent from the above disclosure, and accordingly no further discussion relative to the manner of usage and operation of the instant invention shall be provided. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A permanent magnet which reduces electromagnetic wave emission in electrical appliances with surface displays including but not limited to computer monitors and televisions comprising:

a. four small, single permanent magnets, wherein a positive pole of one magnet is joined with a negative pole of another magnet, and wherein this joined permanent magnet is further attached to another identically joined permanent magnet; and b. a plastic housing having a self-adhesive means, wherein said joined permanent magnet is housed within said housing and wherein said self-adhesive means allows said plastic housing to be mounted to the surfaces of a computer monitor or television set.

2. A permanent magnet as set forth in claim 1, wherein a plurality of said joined permanent magnets housed in said plastic housing is incrementally added to electron gun, cathode ray tube and deflector coil to correspondingly increase the strength and effectiveness of said joined permanent magnets and wherein said increase in the strength and effectiveness of said joined permanent magnets inversely decreases harmful electromagnetic wave emission.

3. A permanent magnet as set forth in claim 1, wherein a plurality of said joined permanent magnets housed in said plastic housing is incrementally added to front and rear of the screen to correspondingly increase the strength and effectiveness of said joined permanent magnets and wherein said increase in the strength and effectiveness of said joined permanent magnets inversely decreases harmful electromagnetic wave emission.

4. A permanent magnet as set forth in claim 1, wherein said small magnets have inherently small electromagnetic fields, wherein said small magnets with their inherently small electromagnetic fields eliminate the possibilities of encroachment into and interference with normal, controlled electromagnetic operations and fields of electrical appliances, wherein said small magnets with their inherently small electromagnetic fields do not introduce detrimental effects on electrical appliances' electron guns, CRT's and screens and wherein said small magnets with their inherently small electromagnetic fields simply reduce the harmful emission of electromagnetic wave from the electron guns, CRT's and screens.

* * * * *